(12) United States Patent
Black

(10) Patent No.: US 6,945,777 B2
(45) Date of Patent: Sep. 20, 2005

(54) FLOSS FOR LIGHT TREATMENT OF ORAL STRUCTURES

(75) Inventor: Michael Black, Foster City, CA (US)

(73) Assignee: Oralum, LLC, Foster City, CA (US)

( * ) Notice: Subject to any disclaimer, the term of this patent is extended or adjusted under 35 U.S.C. 154(b) by 100 days.

(21) Appl. No.: 10/659,527

(22) Filed: Sep. 9, 2003

(65) Prior Publication Data
US 2004/0048224 A1 Mar. 11, 2004

(51) Int. Cl.[7] ............................................. A61C 3/00
(52) U.S. Cl. ........................ 433/29; 132/321; 606/15
(58) Field of Search ......................... 433/29, 215, 216; 132/321, 323, 324, 329; 606/13–16

(56) References Cited

U.S. PATENT DOCUMENTS

| | | | |
|---|---|---|---|
| 5,228,852 A | * 7/1993 | Goldsmith et al. | 433/141 |
| 5,342,198 A | 8/1994 | Vassiliadis et al. | 433/215 |
| 5,435,724 A | 7/1995 | Goodman et al. | 433/215 |
| 5,456,603 A | 10/1995 | Kowlyk et al. | 433/215 |
| 5,795,153 A | 8/1998 | Rechmann | 433/216 |
| 5,957,916 A | * 9/1999 | Jeevanandam et al. | 606/15 |
| 6,019,605 A | 2/2000 | Myers | 433/215 |
| 6,026,828 A | 2/2000 | Altshuler | 132/311 |
| 6,152,951 A | * 11/2000 | Hashimoto et al. | 607/92 |
| 6,569,156 B1 | 5/2003 | Tankovich et al. | 606/10 |
| 6,613,042 B1 | 9/2003 | Tankovich et al. | 606/10 |
| 6,758,844 B2 | 7/2004 | Neuberger | 606/3 |
| 2004/0193236 A1 | 9/2004 | Altshuler et al. | 607/88 |

* cited by examiner

Primary Examiner—Cary E. O'Connor
(74) Attorney, Agent, or Firm—Lumen Intellectual Property Services, Inc.

(57) ABSTRACT

A device for the application of light treatment at a body structure is provided. The device could also be referred to as (dental) floss and be used for body structures in an oral cavity. The device distinguishes a container and a filament. The container hosts one or more light sources each capable of delivering a light beam with a unique light treatment. A user could select between the different light sources and/or parameters. The filament is a strand or fiber of a material transparent to the light beam. The filament is optically connected to a light source (or selected light source) such that the light beam could radiate through the filament at a body structure. The filament could be used in direct or not in direct contact with a body surface as long as the light treatment can be applied to the body structure.

30 Claims, 8 Drawing Sheets

FLOSS FOR LIGHT TREATMENT OF ORAL STRUCTURES

FIELD OF THE INVENTION

This invention relates generally to dental floss. More particularly, the present invention relates to floss capable of providing hygienic effects through the application of light.

BACKGROUND

In general, hygiene relates to the principles of cleanliness, promotion and preservation of health or the freeing from disease-causing microorganisms. Hygienic effects can be established in different ways of which one is through the effect of light on biological structures. For instance, the hygienic effect of visible, near ultraviolet and infrared light on biological structures is known and has been described to provide anti-inflammatory effects, preventative effects, caries-protective effects, plaque-removing effects, teeth-whitening effects, heating effects, anti-bacterial effects, sterilizing effects, cleaning effects, cosmetic effects, therapeutic effects, healing effects, bio-stimulative effects, bio-altering effects, pain-releaving effects, agent-penetrating effects, photo-rejunivating effects and photo-dynamic treatment effects (See for instance a book by *Goldman* (1981) entitled *The biomedical laser: technology and clinical applications* and published by Springer-Verlag, New York; a book by *Katzir* (1993) entitled *Lasers and optical fibers in medicine* and published by Academic Press, New York; a book by *Hajder* et al. (1994) entitled *Acupuncture and lasers* and published by Ming, Belgrade; a book by *Tuner* et al. (1996) entitled *Laser therapy in dentistry and medicine* and published by Prisma Books, Grangesberg, Sweden; a book by *Alster* et al. (1996) entitled *Cosmetic laser surgery* and published by Wiley & Sons, New York; or a book by *Fitzpatrick* et al. (2000) entitled *Cosmetic Laser Surgery* and published by Mosby, St. Louis). The effects of a laser light on biological structures is dependent on the laser properties (active matter, beam wavelength, continuous or impulse mode of operation), characteristics of the structures, water content, pigmentation degree, vascularization, vitality, heterogeneity, specific heat conductivity or time exposure. The photo-effect of a laser can be applied to superficial structures and subcutaneous structures. As far as the mechanisms of laser radiation effects are concerned, they may be thermal, mechanical or chemical.

When it comes to oral hygiene, the art teaches a wide variety of devices with dental floss. Generally, a dental floss contains thread or fibers that is used to remove food particles and plaque from the teeth. Dental floss contributes to the overall hygiene of a persons oral cavity and in particular to the teeth and gums. However, the use of dental floss would not necessarily prevent that person from diseases or health deterioration of the structures in an oral cavity. One of the reasons is that the use of dental floss requires a special technique to ensure that unwanted particles are removed from the teeth instead of being push down towards the gums or left on the teeth. Another reason is the difficulty to assess what has been removed, to determine where the dental floss is at work and to avoid damage to the gums. Yet another reason is that a clean dental floss is required every time a user attempts to remove food particles and plaque from the teeth to avoid accumulation of these unwanted particles on the dental floss. The current use of dental floss results in a timely and sometimes frustrating process, without guaranteed success, that could result in people avoiding flossing their teeth.

The currently available dental floss does not provide any hygienic effect that could be provided by the application of light. Accordingly, there is a need for a new dental floss that would be able to provide light treatment to oral cavities and promote the use of dental floss.

SUMMARY OF THE INVENTION

The present invention provides a device (also referred to as floss or dental floss) for light treatment at a body structure such as an oral cavity. The device includes a container capable of hosting one or more light sources. Each light source is capable of delivering a light beam that provides a light treatment. A filament is optically connected to the light source and stored in the container. The filament is a strand or fiber of a material transparent to the light beam. The filament is thin enough to allow movement of the filament in between teeth. A portion of the filament can be pulled out from the container through an opening in the container and used in direct contact with a body structure or at a distance to the body structure. A means to turn on the light source is used after which the light beam radiates through the pulled out portion of the filament at the body structure.

The light source could be a low power laser, a light emitting diode or a semiconductor laser to provide a light beam from the ultraviolet, visible or infrared spectrum. The types of light treatments that could be selected could include any of the following effects, such as an anti-inflammatory effect, a preventative effect, an anti-bacterial effect, a sterilizing effect, a heating effect, a caries-protective effect, plaque removing effect, a teeth-whitening effect, a cleaning effect, a cosmetic effect, a therapeutic effect, a healing effect, a bio-stimulative effect, a bio-altering effect, a pain-releaving effect, an agent penetrating effect, a photo-rejuvinating effect, a photo-dynamic treatment effect or a tissue stimulating effect. The light source could be controlled in a pulsed manner and a continuous manner. It would also be possible to select one or more parameters of the light source and therewith the light treatment.

In one aspect, the container could include a cutting means to cut the pulled out portion of the filament. In another aspect, the container could include a retracting means to retract a pulled out portion of the filament back into the container. In still another aspect, a holding means could be include to assist in holding the filament for instance during use or to minimize or avoid radiation of the light to the hand or fingers. In still another aspect, a means to close the opening of the container could be included to minimize or avoid dirt or dust entering into the container. In still another aspect, a means to pull out a portion of the filament could be included.

In still another aspect, a selection means to select parameters of the light treatment could be included. The container could include also two or more light sources each capable of delivering a unique light treatment. In this aspect the filament is transparent to the light of each of the two or more light sources. The selection means could then also include means to select one of the two or more light sources. The container includes mechanisms to optically connect the selected light source with the filament.

In yet another aspect the device of the present invention could be combined with a conventional toothpick. The toothpick could also be a toothpick capable of providing a light treatment. Such a toothpick is then optically connected to a light source to radiate a light beam with a light treatment through the toothpick at a body structure. In yet another aspect an agent could be used and applied to the body structure before, during or after the application of the light treatment. Such agents could work as a catalyst, soother or enhancer to the body structure.

BRIEF DESCRIPTION OF THE FIGURES

The objectives and advantages of the present invention will be understood by reading the following detailed description in conjunction with the drawings, in which.

DETAILED DESCRIPTION OF THE INVENTION

Figure 1:
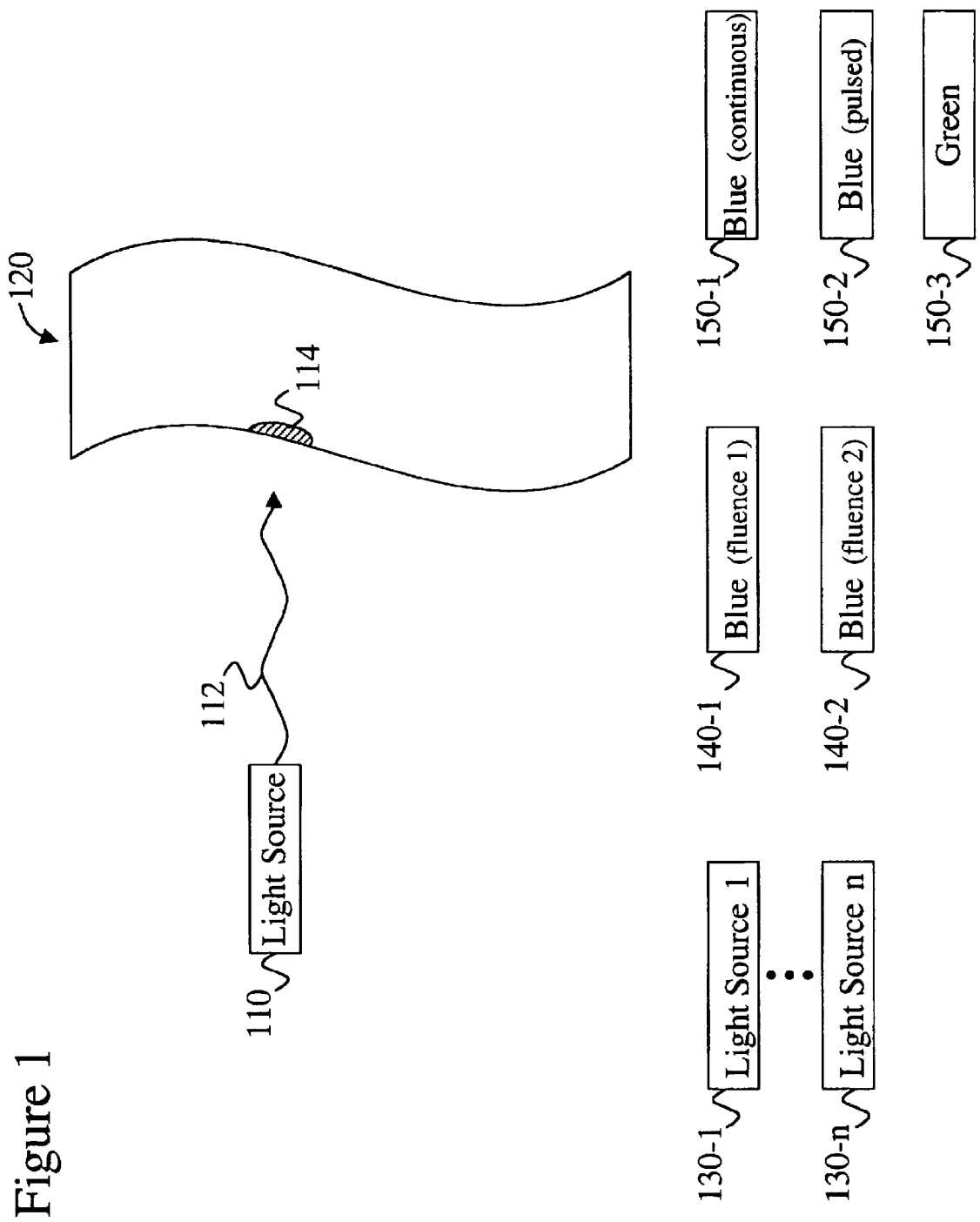
FIG. 1 shows an example of a light treatment at a body structure according to the present invention.

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

The present invention provides a device capable of applying one or more light treatments to body structures such as the ones in an oral cavity. The device is also referred to as a floss or dental floss. These light treatments are established by one or more light sources each capable of delivering a light beam with a unique light treatment to, or in between, the body structures. The application of light treatments could be established either in a quasi-stationary manner or a dynamic manner by moving the filament (See infra for description of filament) with respect to the body structure. The light sources are preferably low power light sources including low power lasers, light emitting diodes or low power semiconductor lasers (See, for instance, the following companies which are listed for purposes of illustration and should not be regarded as limiting to the invention: *Coherent Inc., Santa Clara, Calif.; Microlasers by PolyScientific Inc., Blackbury, Va.; Photonic Products, Bishops Stortford, United Kingdom*; Organic LEDs by *Covion Organic Semiconductors GmbH, Frankfurt, Germany*; Blue light emission from porous silicon by *University of Science and Technology of China in Hefei*). The desired light treatment(s) that one would like to obtain guides the choice of the light source (light sources) and the parameter(s). By varying parameters such as continuous or pulsed (slow or fast), repetition rate, pulse duration different light treatments could be established.

In general, light treatments are defined as treatments with hygienic effects that relate to the cleanliness of these structures, promotion and preservation of health of the structures, freeing the body structure from disease-causing microorganisms or providing therapeutic effects. In particular, the present invention encompasses hygienic effects related to the hygienic effect of visible, near ultra-violet and infrared light on these structures, which are known in the art (for a light spectrum refer to page 13 in a book by *Tuner* et al. (1996) entitled *"Laser therapy in dentistry and medicine"* and published by Prisma Books, Grangesberg, Sweden). Examples of such hygienic effects that could be selected include anti-inflammatory effects, preventative effects, caries-protective effects, plaque-removing effects, teeth-whitening effects, heating effects, anti-bacterial effects, tissue stimulating effects, sterilizing effects, cleaning effects, cosmetic effects, therapeutic effects, healing effects, bio-stimulative effects, bio-altering effects, pain-releaving effects, photo-rejuvination effects, photodynamic effects or agent-penetration effects.

To establish a particular hygienic effect at a body structure one needs to consider the light source properties such as the type of light source, wavelength of the light beam, the continuous or pulse mode (e.g. slow or fast) of operation of the light source, characteristics of the structures, water content of the structures, pigmentation degree of the structures, vascularization of the structures, vitality of the structures, heterogeneity of the structures, specific heat conductivity of the structures, the fluence of light penetration through a structure or the time exposure needed for the light beam. The art provides teachings on hygienic photo-effects of structures including guidelines regarding parameters such as the type of light source, selection of wavelength(s), fluence, penetration, recommended pulse duration, recommended repetition rate, or the like. The selection of the hygienic effect as part of the present invention incorporates these teachings as well as new teachings that become available in the art describing newly identified hygienic effects.

Currently available teachings are described in the following books, which provide an exemplary list rather than a comprehensive list. The list includes a book by *Goldman* (1981) entitled *"The biomedical laser: technology and clinical applications"* and published by Springer-Verlag, New York; a book by *Katzir* (1993) entitled *"Lasers and optical fibers in medicine"* and published by Academic Press, New York; a book by *Hajder* et al. (1994) entitled *"Acupuncture and lasers"* and published by Ming, Belgrade; a book by *Tuner* et al. (1996) entitled *"Laser therapy in dentistry and medicine"* and published by Prisma Books, Grangesberg, Sweden; a book by *Alster* et al. (1996) entitled *"Cosmetic laser surgery"* and published by Wiley & Sons, New York; or a book by *Fitzpatrick* et al. (2000) entitled *"Cosmetic Laser Surgery"* and published by Mosby, St. Louis).

FIG. 1 shows an exemplary embodiment of a light source 110 delivering a light beam with a wavelength 112. The wavelength 112, e.g. a green wavelength, provides a unique hygienic effect when applied to body structure 120. In this example, light beam 112 has a fairly superficial hygienic effect at body structure 120 as shown by 114. The present invention is not limited to a superficial effect and could also penetrate to deeper levels. In general, n light sources 130-1 to 130-n could be provided from which a user can select one light source at a time. In one example, two of the same light sources could be provided such as two light sources 140-1, 140-2 that each deliver blue light, however, with at least one different parameter to establish a different and unique hygienic effect for each of the two light sources 140-1, 140-2 that can be selected by a user. The different and unique hygienic effect in this example was established by different fluences for each of the two light sources 140-1, 140-2, i.e. fluence 1 and fluence 2, respectively. In another example three light sources could be provided, of which two are the same 150-1, 150-2 and one 150-3 is different, though all three delivering a unique hygienic effect. The different and unique hygienic effect in this example between 150-1, 150-2 was established by having the same light source 150-1 and 150-2 but with a different mode such as continuous mode or pulsed mode respectively.

Figure 2:
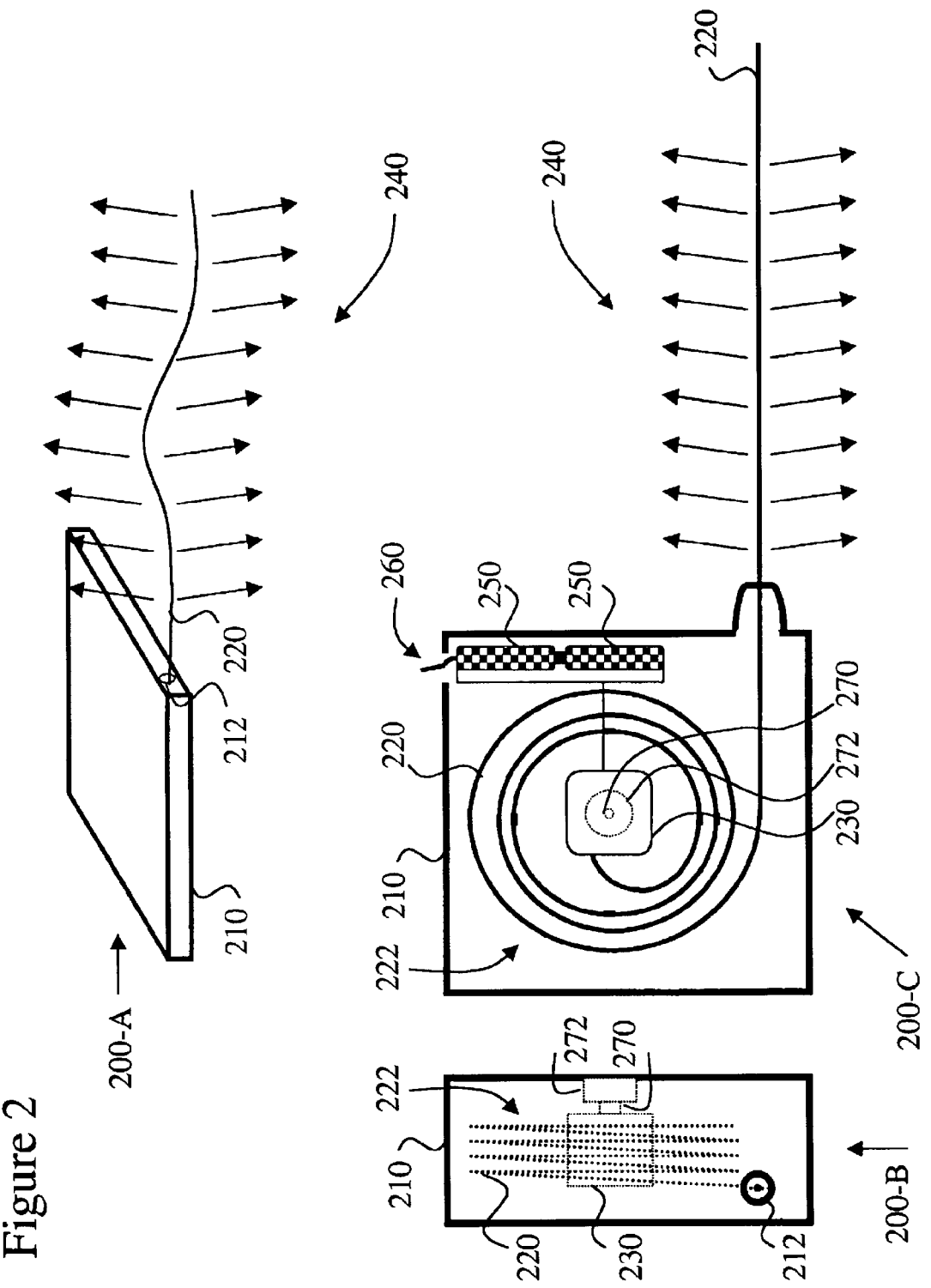
FIG. 2 shows an example of a device according to the present invention.

FIG. 2 shows an example of a device that includes a container 210 and a filament 220 (200-A, 200-B, 200-C are different perspective views of the same device). Container 210 hosts a light source 230, which is capable of delivering a light beam 240. Light source 230 is powered by a power supply 250, such as a (rechargeable) battery. Power supply 250 is connected to a means to turn on light source 230 shown in this example as a switch 260. Switch 260 is preferably positioned at the outside of container 210 (e.g. at a side or bottom) and controls the on/off stage of power supply 250 and therewith the on/off stage of light source 230.

Filament 220 is optically connected to light source 230. Filament 220 is a strand or fiber of a material transparent to the light beam produced by light source 230. The filament is thin enough and flexible enough to allow movement of the filament in between the teeth. Examples of filaments are for instance, but not limited to, soft fibers, doped fibers (silicone or latex doped), colored or colorless fibers, or the like. Once filament is illuminated, it becomes a glowing filament that radiates a selected light treatment. Generally speaking, the light beam radiates through the surface of the transparent filament and could be used at a distance or in direct contact with a body structure.

Figure 3:
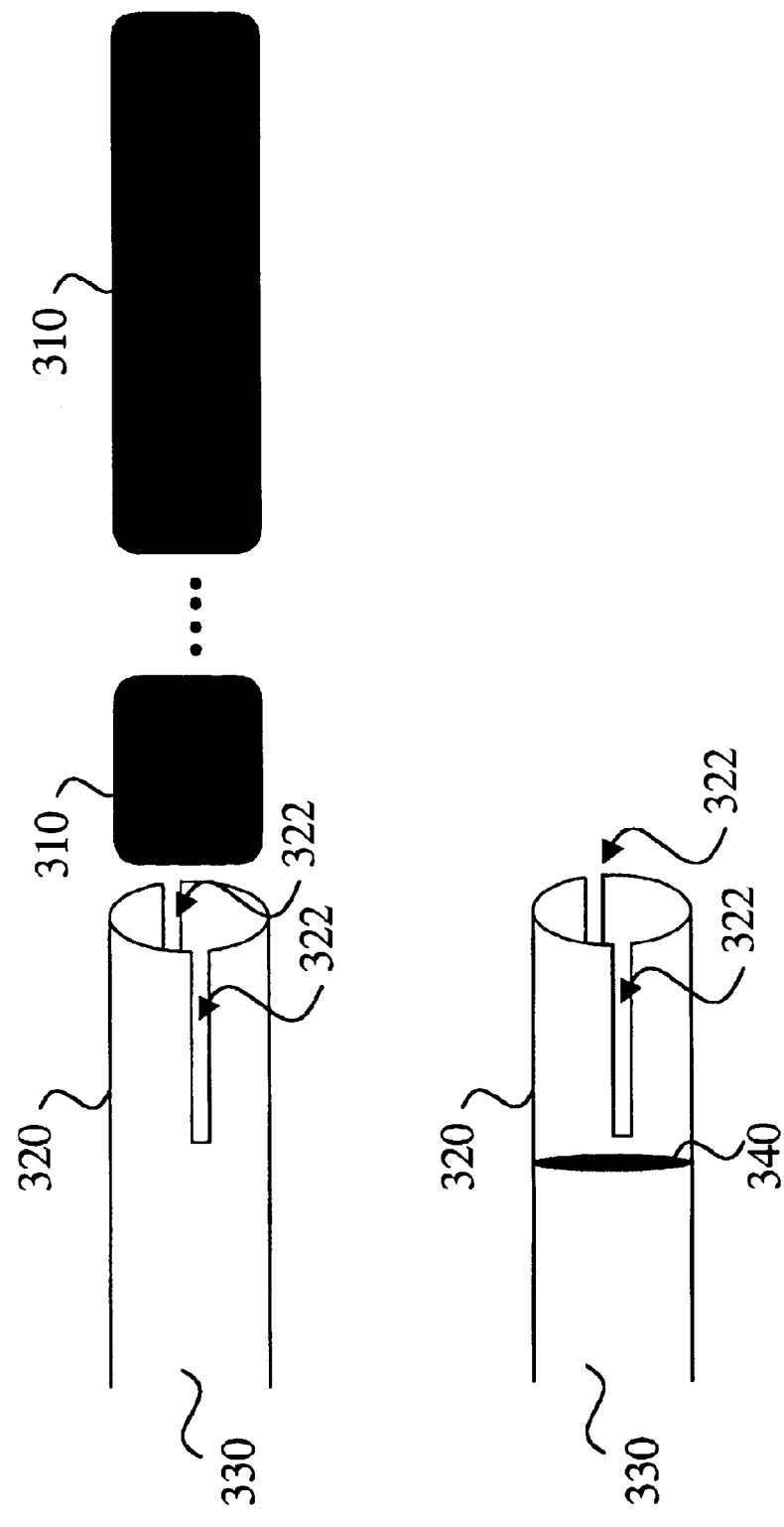
FIG. 3 shows an example of an optical connection between the light source and the filament according to the present invention.

FIG. 3 shows an example of how filament 310 could be placed inside a holder 320 to align the output of light source 330 with filament 310. The position of filament 310 inside holder 320 could for instance be ensured by squeezing holder 320 so that openings 322 come closer together. In one aspect, one or more optical elements (e.g. a (collimator) lens 340) could be used to promote that the light beam travels from light source 330 into filament 310.

Figure 4:
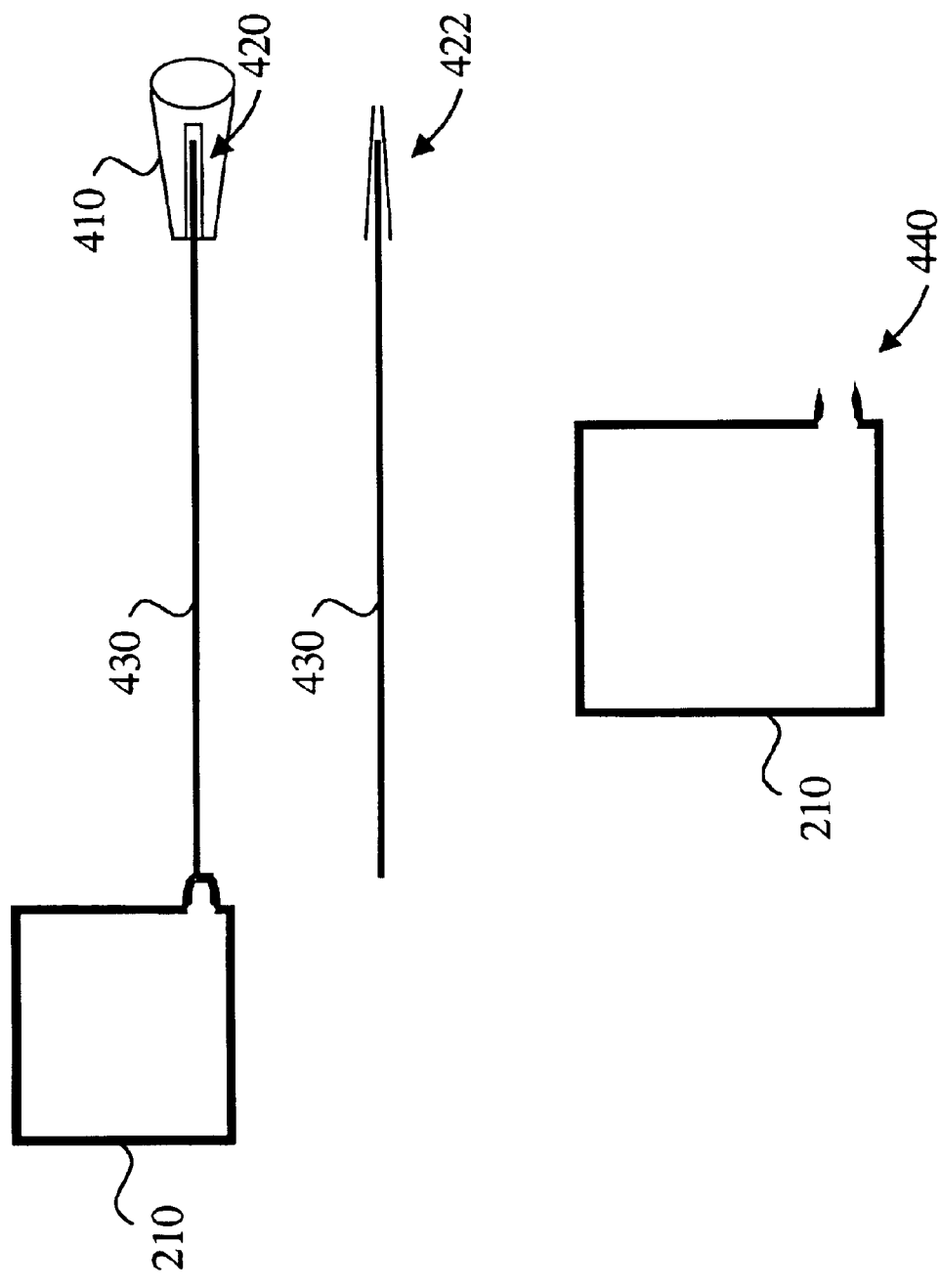
FIG. 4 shows an example of a means to hold the filament, a means to pull out the filament or a means to close the opening of the container according to the present invention.

Filament 220 is stored in container 210, preferably as a spool 222. However, filament 220 is not limited to be stored as a spool and could be stored in any other way as long as filament 220 can be optically connected to light source 230 and can be pulled out from container 210 through opening 212. In one aspect, a means could be included to hold filament 220, then referred to as a holding means 410 as shown in FIG. 4. The holding means could provide a user with a convenient device that could make the application of the filament easier. The holding means could be made out of a non-transparent material (at least to the selected light beam) to avoid radiation to a user's hand or fingers. The holding means could take any shape and is not limited to the shape of holding means 410 as shown in FIG. 4. However, it would be preferred to have an ergonomically shaped holding means that easily fits a user's hand. Different shapes and sizes would then accommodate the shapes and sizes of the hands of children and adults. Holding means 410 could include an easy quick-connect or clip 420 to connect to filament 430 which are known in the art. Open position 422 allows filament 430 to enter quick-connect or clip 420. In one aspect, holding means could be used as a means to pull out a portion of the filament from the container. In another aspect holding means could be used as a lid 440 to close opening 212 to prevent dirt or dust to enter container 210. The means to hold, pull and close can be the same elements, all combined in one, or could be separate elements that could be used in combination with the container and filament.

In the example of FIG. 2, light source 230 is placed on a rod 270 that rotates inside or around 272 when filament 220 is pulled out from container 210. In one aspect, rod 270 could include a mechanism that retracts the pulled out portion of filament 220 back into container 210. Such retraction means are known in the art (e.g. used in tape measures, cable devices, or the like). Typically a push on a button enables the retraction means to release its holding position and retract the pulled out portion of filament 220. For obvious reasons, if a retraction means is used one would need to consider that the end of the filament remains outside of the container. A holding means or a lid holding the filament would be preferred so that the next time the user wants to use the filament it can easily be pulled out from the container.

Figure 5:
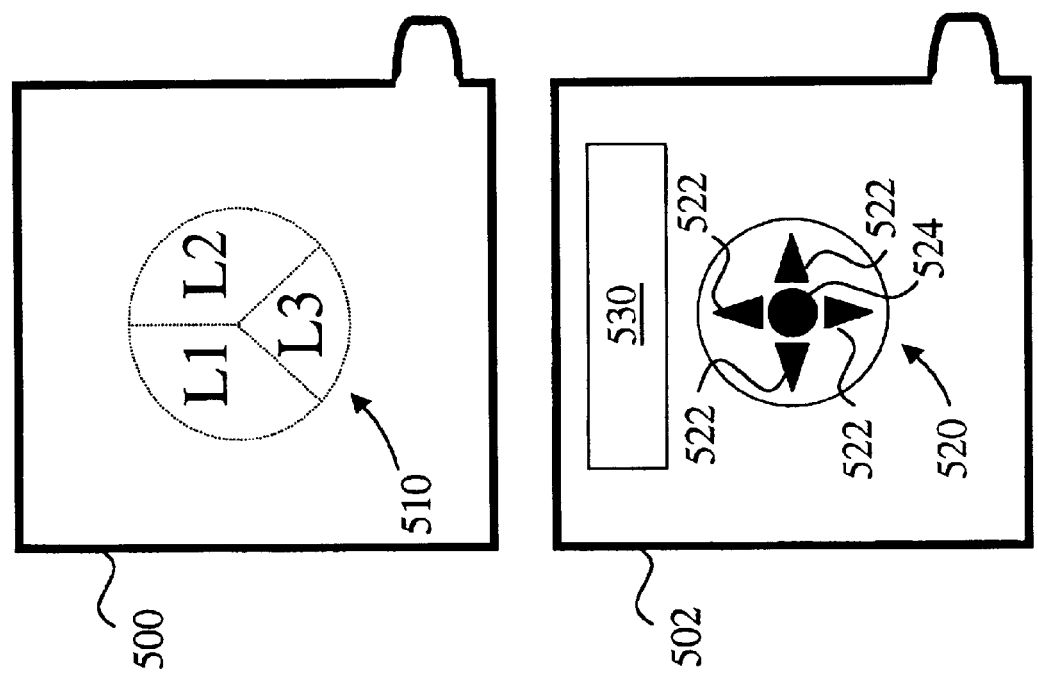
FIG. 5 shows an example of multiple light sources and a selection means according to the present invention.

As discussed supra, more than one light treatment could be selected. FIG. 5 shows an example of a container 500 hosting and capable of selecting three light sources 510 (L1, L2, L3) each with a unique light beam and light treatment. Each light source L1, L2, L3 could be selected and the selected light source is then optically connected to the filament for instance by a turning knob, by an automated system, a switch, a motor, or the like. One could consider different ways to optically connect or align the selected light source to the filament as well as different optical elements to promote and/or ensure proper light guidance through the filament if needed.

A selection means 520 could be included with container 502 which could have, for instance, four arrow buttons 522 and one center button 524. Each arrow button 522 corresponds to a light source, parameter or mode that could be selected. The selection could be assisted by a displaying means 530 (optional) that provides feedback to the user about the selections or current modes of operation(s). The center button 524 could be used as a confirmation button, a turn on/off button or the like. The up, down, left and right arrow buttons could relate to the browsing or selection on the displaying means 530.

Displaying means 530 could be any type or size of displaying means that would fit the container and is useful to the user. Necessary software and hardware components would be included to provide the functionality to display the parameters, selections and/or functions as well as provide functionality to the buttons.

Figure 6:
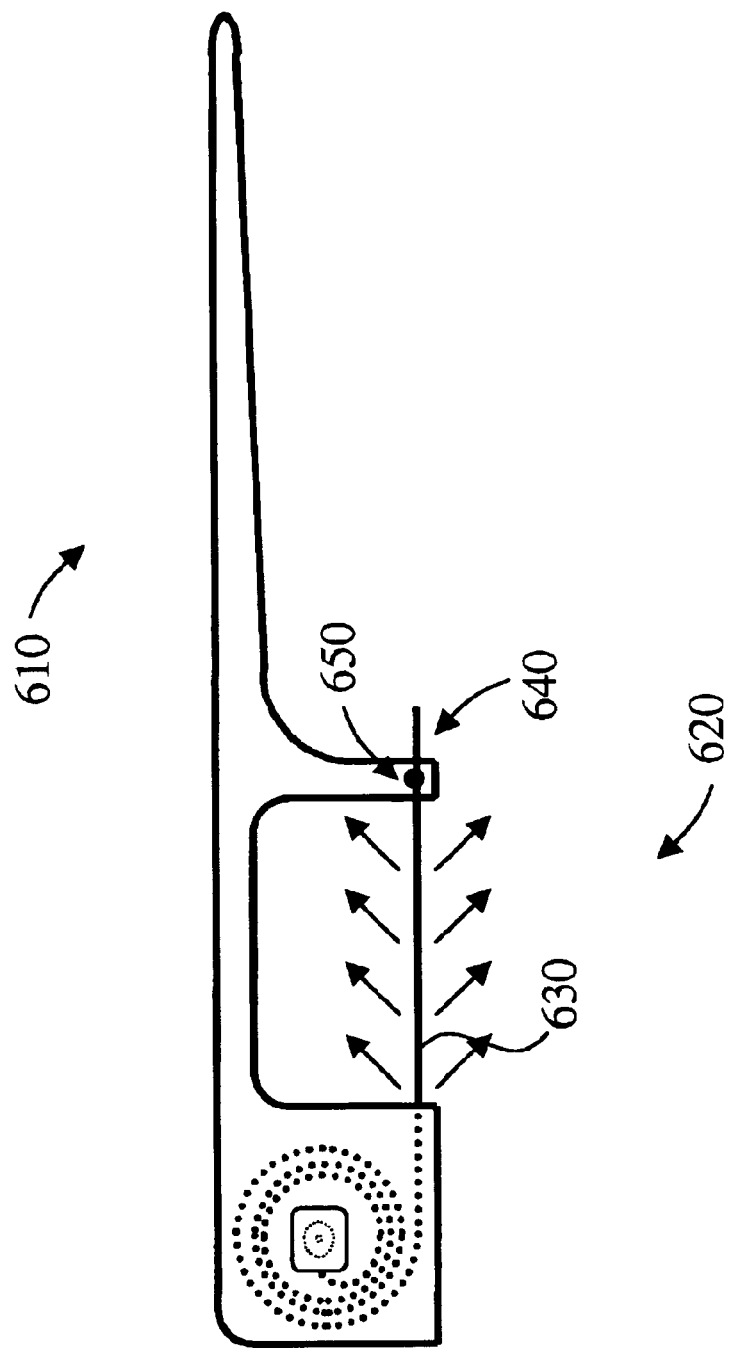
FIG. 6 shows an example of a floss combined with a toothpick according to the present invention.
Figure 7:
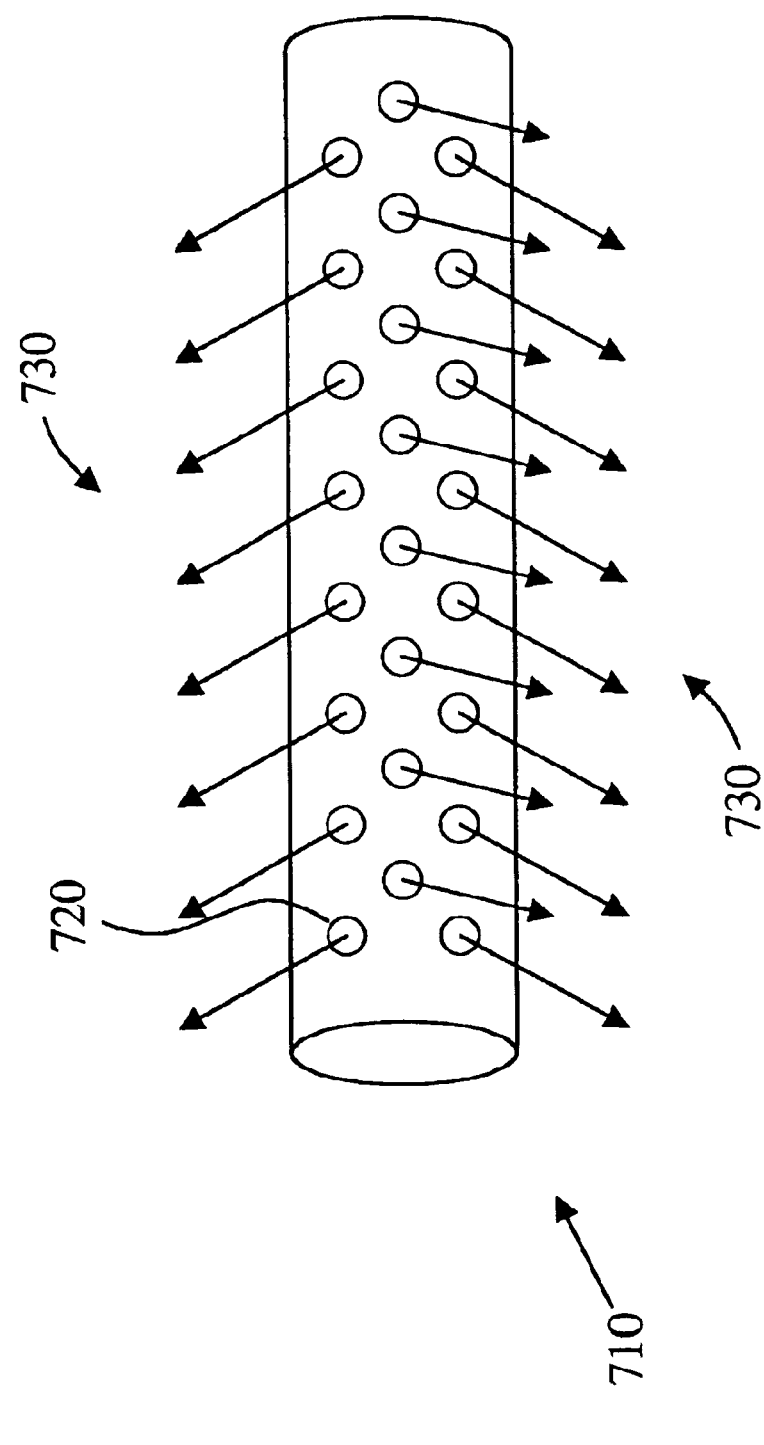
FIG. 7 shows an example of a flexible waveguide according to the present invention.
Figure 8:
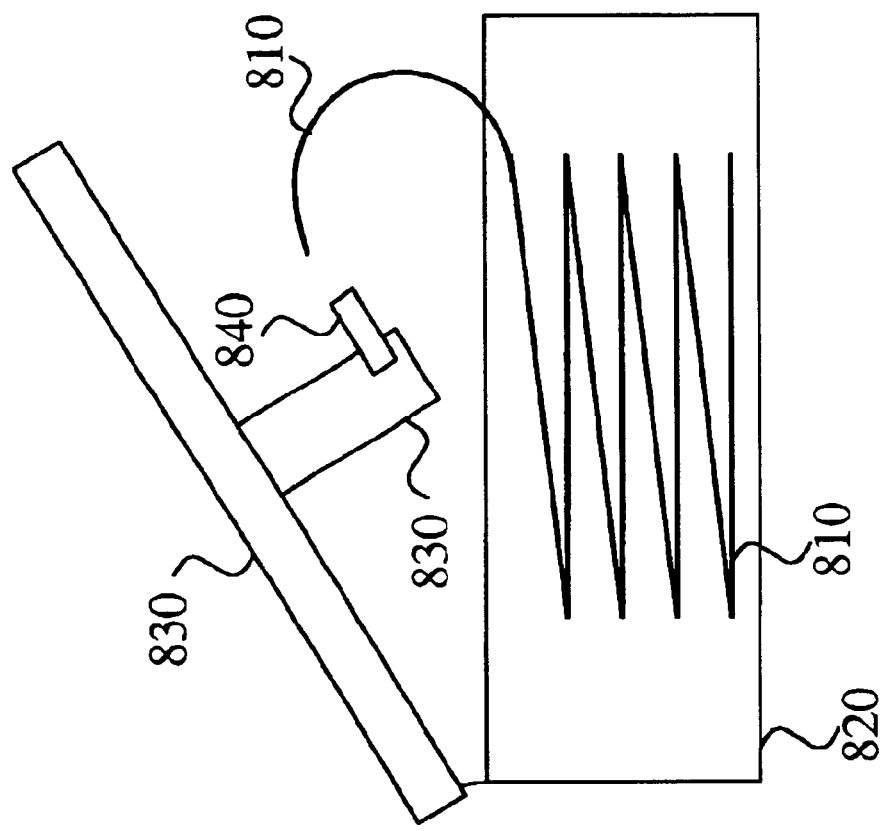
FIG. 8 shows an example of a container with a lid according to the present invention.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. In one variation as shown in FIG. 6 a toothpick 610 could be added to device 620, device 620 is similar to the device as taught supra. Filament 630 could be pulled through opening 640 (in plane of drawing) and potentially held in place by for instance a spring-loaded pin 650. The toothpick could be a regular toothpick as know in the art or a toothpick that could be optically connected to a light source and therewith providing a light treatment (See U.S. patent application Ser. No. 10/645,674 entitled "*A toothpick for light treatment of body structures*" by the same inventor as the present application with filing date Aug. 20, 2003 for teachings of such a toothpick, which is hereby incorporated for all that it discloses). The light source optically connected to the toothpick could be a separate light source with its own control or could be the same light source as for the filament. In case a different light source is used for the toothpick, there is a choice whether the same or a different light treatment for the toothpick could be used compared to the light treatment for the filament. In any event, the toothpick would glow when illuminated by a light beam from a light source. In another variation a flexible waveguide 710 could be used instead of a filament as shown in FIG. 7. The difference between the flexible waveguide and the filament is that the flexible waveguide is not necessarily transparent and could therefore include openings 720 to allow passage of light 730. In still another variation the filament is a removable, a disposable, a reusable or a replaceable filament. The filament 810 could be placed in container 820 by opening and closing lid 830 of container 820 as shown in FIG. 8. Once filament 810 is placed inside container 820, it can be optically connected to light source 830 through connection 840 (See also FIG. 3). Light source 830 could be pivotally placed or connected to lid 830 to allow the spool of filament to easily unroll when pulled out. In still another variation an agent could be used and applied to the body structures before, during or after the application of the light treatment. Examples of agents are for instance bioprotective agents, photocatalyst, treatment gels or cream, soothing agents, tissue permeation enhancers or the like (See, for instance, the following companies/products which are listed solely for purposes of illustration and should not be regarded as limiting to the invention: *Neova by Procyte Corp. www.procyre.com; Medicalia Inc. www.medicalia.com; or ESBA Laboratories Inc.*). Such agents could work as a catalyst, soother or enhancer to the body structures. All such variations are considered to be within the scope and spirit of the present invention as defined by the following claims and their legal equivalents.

What is claimed is:

1. A device for light treatment at a body structure, comprising:
    (a) a container, wherein said container comprises a light source capable of delivering a light beam, wherein said light beam provides said light treatment;
    (b) a filament optically connected to said light source and stored in said container, wherein said filament is a strand or fiber of a material transparent to said light beam, and wherein a portion of said filament can be pulled out from said container; and
    (c) a means to turn on said light source after which said light beam radiates through said pulled out portion of said filament at said body structure.

2. The device as set forth in claim 1, wherein said filament is a removable, a disposable, a reusable or a replaceable filament.

3. The device as set forth in claim 1, wherein said filament is thin enough and flexible enough to allow moving said filament in between teeth.

4. The device as set forth in claim 1, wherein said light source is a low power laser, a light emitting diode or a semiconductor laser.

5. The device as set forth in claim 1, further comprising a cutting means to cut said pulled out portion of said filament.

6. The device as set forth in claim 1, further comprising a retracting means to retract said pulled out portion of said filament.

7. The device as set forth in claim 1, further comprising a means to hold said pulled out portion of said filament.

8. The device as set forth in claim 1, further comprising a means to close an opening of said container through which said filament can be pulled out.

9. The device as set forth in claim 1, further comprising a means to pull out said portion of said filament.

10. The device as set forth in claim 1, further comprising a selection means to select parameters of said light treatment.

11. The device as set forth in claim 1, wherein said container comprises two or more light sources each capable of delivering a unique light treatment through said filament, said filament is transparent to the light of each of said two or more light sources, and further comprising a selection means to select one of said two or more light sources and said selected light source being optically connectable to said filament.

12. The device as set forth in claim 1, wherein said light treatment is selected from the group consisting of an anti-inflammatory effect, a preventative effect, an anti-bacterial effect, a sterilizing effect, a heating effect, a caries-protective effect, plaque removing effect, a teeth-whitening effect, a cleaning effect, a cosmetic effect, a therapeutic effect, a healing effect, a bio-stimulative effect, a bio-altering effect, a pain-releaving effect, an agent penetrating effect, a photo-rejuvinating effect, a photo-dynamic treatment effect or a tissue stimulating effect.

13. The device as set forth in claim 1, wherein said light beam comprises light from the ultraviolet, visible or infrared spectrum.

14. The device as set forth in claim 1, wherein said light beam can be selected to be applied in a manner selected from the group consisting of a pulsed manner and a continuous manner.

15. The device as set forth in claim 1, further comprising a toothpick.

16. The device as set forth in claim 15, wherein said toothpick is a transparent toothpick and wherein said transparent toothpick is optically connected to said light source or said transparent toothpick is optically connected to a different light source.

17. A device for light treatment at a body structure, comprising:
    (a) a container, wherein said container comprises a light source capable of delivering a light beam, wherein said light beam provides said light treatment;
    (b) a flexible waveguide optically connected to said light source and stored in said container, wherein said flexible waveguide comprises openings to allow radiation of said light beam, and wherein a portion of said flexible waveguide can be pulled out from said container; and
    (c) a means to turn on said light source after which said light beam radiates through said openings of said pulled out portion of said flexible waveguide at said body structure.

18. A method to optically apply a light treatment at a body structure, comprising the steps of:
    (a) optically connecting filament to two or more light sources each capable of delivering a unique light beam, wherein said filament is a strand or fiber of a material transparent to each of said light beams;
    (b) pulling out a portion of said filament from a container that hosts said filament;
    (c) placing said pulled out portion of said filament near or against said body structure; and
    (d) selecting one of said two or more light sources, optically connecting said selected light source to said filament and turning on said selected light source after which said light beam of said selected light source radiates through said pulled out portion of said filament at said body structure.

19. The method as set forth in claim 18, further comprising the step of cutting said pulled out portion of said filament.

20. The method as set forth in claim 18, further comprising the step of holding said pulled out portion of said filament with a holding means.

21. The method as set forth in claim 18, further comprising the step of closing the opening of said container through which said filament can be pulled out.

22. The method as set forth in claim 18, further comprising an step of pulling out said portion of said filament with a holding means or a closing means.

23. The method as set forth in claim 18, further comprising the step of retracting said pulled out portion of said filament back into said container.

24. The method as set forth in claim 18, further comprising the step of selecting parameters of said light treatment.

25. The method as set forth in claim 18, wherein said light treatment is selected from the group consisting of an anti-inflammatory effect, a preventative effect, an anti-bacterial effect, a sterilizing effect, a heating effect, a caries-protective effect, plaque removing effect, a teeth-whitening effect, a cleaning effect, a cosmetic effect, a therapeutic effect, a healing effect, a bio-stimulative effect, a bio-altering effect, a pain-releaving effect, an agent penetrating effect, a photo-rejuvinating effect, a photo-dynamic treatment effect or a tissue stimulating effect.

26. The method as set forth in claim 18, wherein said light beam comprises light from the ultraviolet, visible or infrared spectrum.

27. The method as set forth in claim 18, wherein said light beam can be selected to be applied in a manner selected from the group consisting of a pulsed manner and a continuous manner.

28. The method as set forth in claim 18, further comprising a toothpick.

29. The method as set forth in claim 28, wherein said toothpick is a transparent toothpick and wherein said transparent toothpick is optically connected to said light source or said transparent toothpick is optically connected to a different light source.

30. The method as set forth in claim 18, further comprising the step of adding an agent to said body structure.

* * * * *